United States Patent
Lee et al.

(10) Patent No.: US 8,814,803 B2
(45) Date of Patent: Aug. 26, 2014

(54) PORTABLE DEVICE FOR MEASURING USER'S BIOSIGNALS AND THE METHOD THEREOF

(75) Inventors: Jong Youn Lee, Yongin-si (KR);
Kenichi Yamakoshi, Kanazawa (JP);
Kun Soo Shin, Seongnam-si (KR);
Shinobu Tanaka, Kanazawa (JP);
Takehiro Yamakoshi, Kanazawa (JP)

(73) Assignee: Samsung Electronics Co., Ltd., Suwon-Si (KR)

( * ) Notice: Subject to any disclaimer, the term of this patent is extended or adjusted under 35 U.S.C. 154(b) by 875 days.

(21) Appl. No.: 11/984,103

(22) Filed: Nov. 13, 2007

(65) Prior Publication Data
US 2008/0177187 A1    Jul. 24, 2008

(30) Foreign Application Priority Data
Jan. 19, 2007 (KR) .......... 10-2007-0006301

(51) Int. Cl.
*A61B 5/0225* (2006.01)
(52) U.S. Cl.
USPC .......... 600/503; 600/490
(58) Field of Classification Search
USPC .......... 600/485, 490, 503, 499, 492, 495
See application file for complete search history.

(56) References Cited

U.S. PATENT DOCUMENTS

| | | | |
|---|---|---|---|
| 4,896,676 A * | 1/1990 | Sasaki | 600/494 |
| 5,201,758 A * | 4/1993 | Glover | 606/202 |
| 6,290,650 B1 * | 9/2001 | Butterfield et al. | 600/485 |
| 6,432,060 B1 * | 8/2002 | Amano | 600/490 |
| 6,443,906 B1 * | 9/2002 | Ting et al. | 600/490 |
| 6,514,212 B1 * | 2/2003 | Ide et al. | 600/490 |
| 6,932,773 B2 * | 8/2005 | Inoue et al. | 600/499 |
| 7,101,338 B2 * | 9/2006 | Yang | 600/485 |
| 7,306,563 B2 * | 12/2007 | Huang | 600/500 |
| 2002/0077558 A1 * | 6/2002 | Itonaga et al. | 600/490 |
| 2004/0044288 A1 * | 3/2004 | Gorenberg et al. | 600/481 |
| 2004/0044290 A1 * | 3/2004 | Ward et al. | 600/490 |
| 2005/0256411 A1 * | 11/2005 | Yang | 600/490 |
| 2005/0283084 A1 * | 12/2005 | Kato | 600/499 |
| 2006/0052712 A1 * | 3/2006 | Poliac et al. | 600/490 |
| 2006/0079792 A1 * | 4/2006 | Finburgh et al. | 600/485 |

FOREIGN PATENT DOCUMENTS

| | | |
|---|---|---|
| JP | 11-299745 | 11/1999 |
| JP | 11-318836 | 11/1999 |
| JP | 2002-191567 | 7/2002 |
| JP | 2003-144397 | 5/2003 |
| JP | 2003-144398 | 5/2003 |
| JP | 2004-215915 | 8/2004 |
| KR | 10-2006-0070451 | 6/2006 |

OTHER PUBLICATIONS

Office Action issued in corresponding Korean Patent Application No. 10-2007-0006301; mailed on Mar. 13, 2008.

* cited by examiner

*Primary Examiner* — Jacqueline Cheng
*Assistant Examiner* — Michael Catina
(74) *Attorney, Agent, or Firm* — Staas & Halsey LLP

(57) ABSTRACT

A portable biosignal measurement apparatus and the method is provided. The apparatus includes: a micro pump; a pressure supplier including a cuff which applies a pressure in a direction of a radial artery of a user's wrist by a fluid, which is flowed depending on pressure provided by the micro pump; and a sensor unit to measure a biosignal using displacement of the radial artery.

17 Claims, 5 Drawing Sheets

PORTABLE DEVICE FOR MEASURING USER'S BIOSIGNALS AND THE METHOD THEREOF

CROSS-REFERENCE TO RELATED APPLICATIONS

This application claims the benefit of Korean Patent Application No. 10-2007-0006301, filed on Jan. 19, 2007, in the Korean Intellectual Property Office, the disclosure of which is incorporated herein by reference.

BACKGROUND

1. Field

Embodiments relate to a portable biosignal measurement apparatus, and more particularly, to a portable biosignal measurement apparatus which can apply pressure to only a radial artery area of a user's wrist using a micro pump and a cuff, thereby measuring a biosignal of the user.

2. Description of the Related Art

Currently, various types of portable blood pressure measurement apparatuses are developed and utilized to measure the blood pressure. Particularly, a blood pressure measurement apparatus in a form of a wristwatch is widely utilized due to its convenient portability. As an example, a portable pressure measurement apparatus is constructed from an air bag as a band in a form of a wristwatch worn around the wrist. The portable blood pressure measurement apparatus pressurizes the air bag using a mini-pump and measures a changing pulse waveform pattern via a pressure sensor. However, in the portable blood pressure measurement apparatus constructed as above, when pressurizing the air bag, a user may feel strong pressure around the wrist and thus, feel some discomfort. Specifically, the portability is reduced due to the air bag.

Also, a blood pressure measurement apparatus using a tonometry instrument is utilized. The blood pressure measurement apparatus is in a form of a wristwatch where a sensor is provided between the muscle and bone of the wrist, and measures the blood pressure by supplying a minimal amount of pressure to an artery of the wrist. In this case, the pressure to be applied to the wrist may be reduced, but the sensor must be closely attached to the artery by injecting the air from the outside. Thus, the user may not readily carry the blood pressure measurement apparatus. Also, since the air bag and the sensor are comparatively large, an external pressure generator is required and thus, the portability of the blood pressure measurement apparatus may not be actually achieved.

Also, when a user presses a sensor and the pressure is transmitted to the radial artery, the radial artery becomes flat. Thus, a portable blood pressure measurement apparatus both analyzing a pulse waveform, which incurs in the above-described situation, and measuring the blood pressure is utilized. It is advantageous in that a user can carry the portable blood pressure measurement apparatus, but it is complex in that the user has to keep pressing the sensor by hand to generate the pressure. Also, the portable blood pressure measurement apparatus is generally manufactured in a large size and thus, the user may not wear the portable blood pressure measurement apparatus.

As described above, a blood pressure measurement apparatus according to the conventional art applies pressure around the wrist to measure a blood pressure. Thus, a user may have great inconvenience to repeatedly measure the blood pressure using the blood pressure measurement apparatus. Also, since the blood pressure measurement apparatus is generally manufactured in a large size, the user may not readily wear the blood pressure measurement apparatus. Accordingly, a portable biosignal measurement apparatus which a user can readily carry at all times to accurately measure a biosignal, such as a blood pressure, and the like, is required.

SUMMARY

Additional aspects and/or advantages will be set forth in part in the description which follows and, in part, will be apparent from the description, or may be learned by practice of the invention.

An aspect of the present invention provides a portable biosignal measurement apparatus which can measure a biosignal by applying pressure to only a radial artery area of a user's wrist using a micro pump and a cuff, thereby improving a user convenience.

An aspect of the present invention also provides a biosignal measurement apparatus which a user can readily carry, since the size of the biosignal measurement apparatus is minimized, thereby conveniently and constantly measuring a biosignal.

According to an aspect of the present invention, there is provided a portable biosignal measurement apparatus, the apparatus including: a micro pump; a pressure supplier including a cuff which applies pressure in a direction of a radial artery of a user's wrist by a fluid, which is flowed depending on pressure provided by the micro pump; and a sensor unit to measure a biosignal using displacement of the radial artery.

Additional aspects, features, and/or advantages of the invention will be set forth in part in the description which follows and, in part, will be apparent from the description, or may be learned by practice of the invention.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION OF THE EMBODIMENTS

Figure 1A:
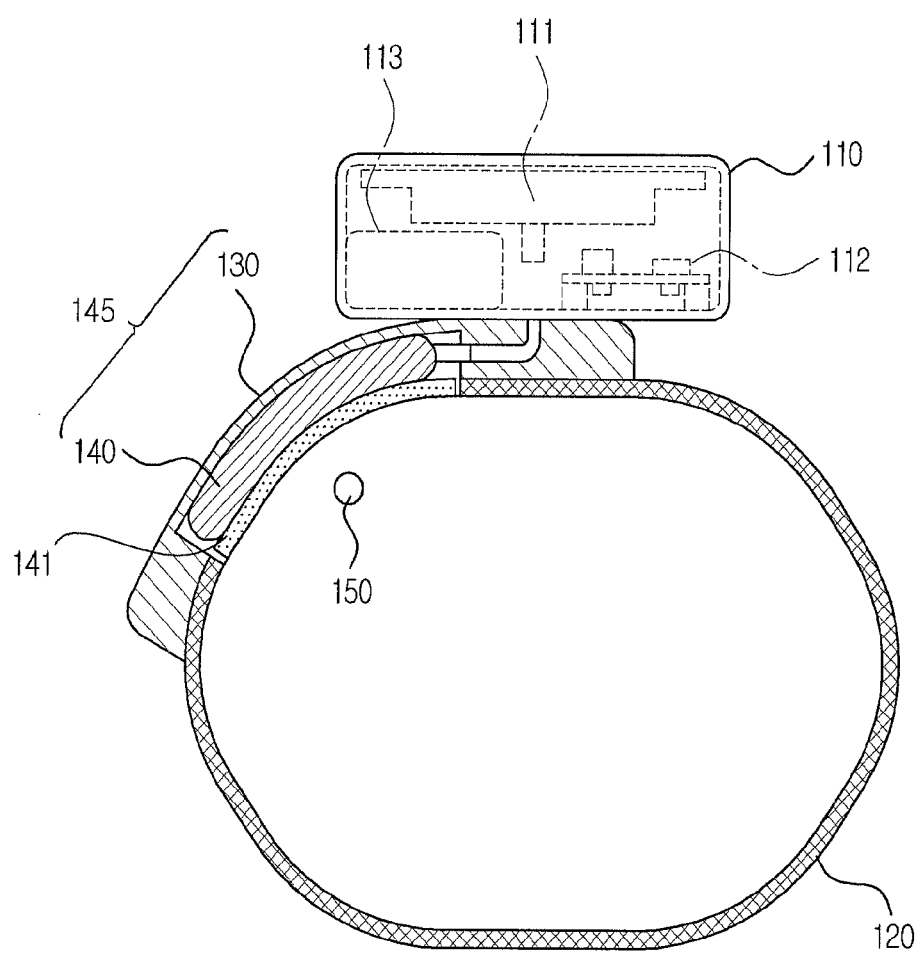
FIG. 1A is a diagram illustrating a configuration of a portable biosignal measurement apparatus before pressure is applied according to an exemplary embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

A portable biosignal measurement apparatus according to the present invention may be configured into an element of an accessory which is wearable around a wrist, such as a wristwatch, a bracelet, and the like. Also, the biosignal measurement apparatus may be configured into a unit article such as a bracelet. In the present specification, when the biosignal measurement apparatus is configured into the form of a bracelet will be described as an example, for convenience of description.

The portable biosignal measurement apparatus is also wearable around a user's wrist, and may measure various types of biosignals, such as the user's pulse wave, blood pressure, and the like. In the present specification, an exemplary embodiment in which the biosignal measurement apparatus is wearable around the user's wrist, and measures the user's blood pressure, will be described, for convenience of description.

Hereinafter, a portable biosignal measurement apparatus and method according to exemplary embodiments of the present invention will be described in detail with reference to the accompanying drawings.

FIG. 1A is a diagram illustrating a configuration of a portable biosignal measurement apparatus before pressure is applied according to an exemplary embodiment of the present invention.

The portable biosignal measurement apparatus according to the present exemplary embodiment of the present invention may include a control unit 110, a pressure supplier 145 including a supporting member 130 and a cuff 140, a sensor unit 141, and a fastening unit 120.

The control unit 110 includes a micro pump 111, a measurement control unit 112, and a vessel 113.

The micro pump 111 applies pressure so that a fluid contained in the vessel 113 may flow into the cuff 140 of the pressure supplier 145. The fluid is a concept including a gas or a liquid which is easily transferred, compared with a solid, may be contained in any shape, and has a feature of freely flowing. The micro pump 111 may include a small motor unit designed to generate pressure.

The vessel 113 contains the fluid, and controls the fluid to flow into the cuff 140 by pressure which the micro pump 111 applies. A pipe unit (not illustrated) may be additionally included between the vessel 113 and the cuff 140 so that the fluid may easily flow into the cuff 140, and the present invention may be embodied so that pressure of air applied by the micro pump 111 without the vessel 113 may be directly flowed into the cuff 140 when the fluid is air (not illustrated).

Figure 1B:
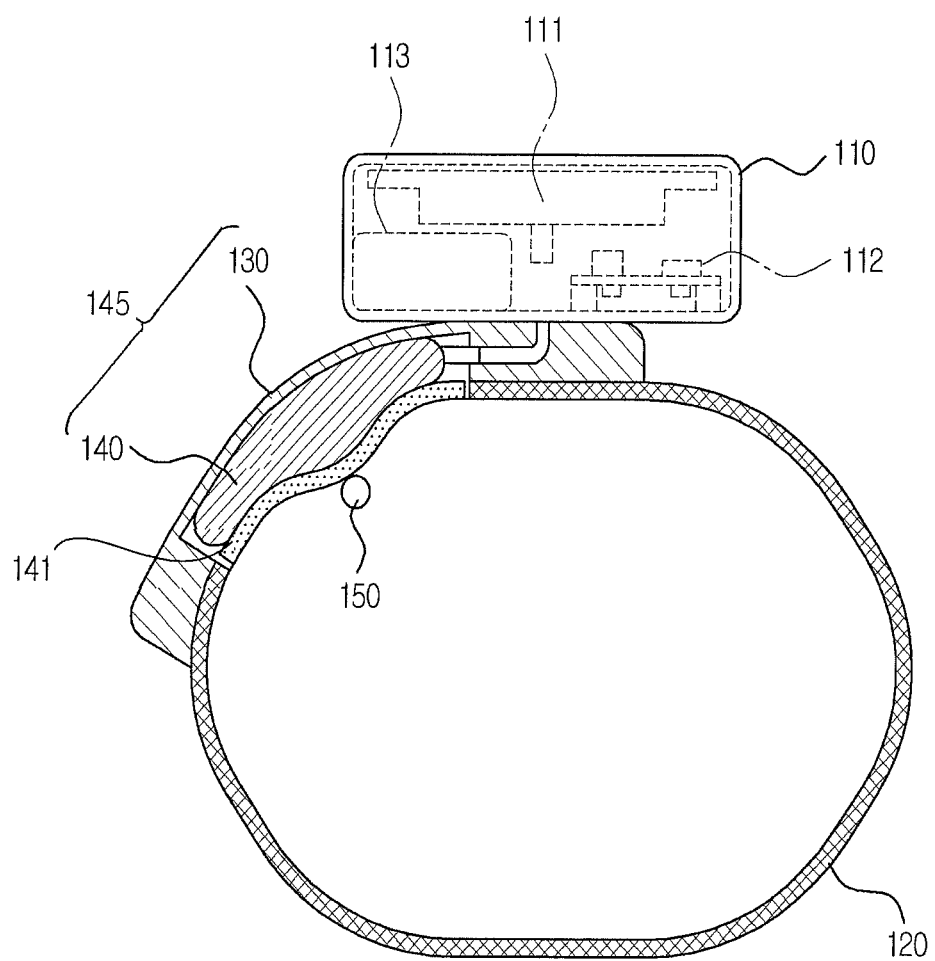
FIG. 1B is a diagram illustrating a configuration of a portable biosignal measurement apparatus when pressure is applied according to an exemplary embodiment of the present invention.

FIG. 1B is a diagram illustrating a configuration of a portable biosignal measurement apparatus when pressure is applied according to an exemplary embodiment of the present invention.

Referring to FIG. 1B, a fluid of a vessel 113 is flowed into a cuff 140 of a pressure supplier 145 by pressure which a micro pump 111 applies. The cuff 140 in which the fluid is flowed, swells depending on a flowed fluid amount, and pressure is applied to a radial artery 150 of a user's wrist due to swelling of the cuff 140. A supporting member 130 supports an upper surface and a lateral surface of the cuff 140 so that the cuff 140 may apply pressure in a direction of the radial artery 150 of the user's wrist. The cuff 140 may be swollen to the radial artery 150 area of the user's wrist due to support of a supporting member 130

Data used for biosignal measurement is input from a sensor unit 141, measuring a user's biosignal, to a measurement control unit 112, and the measurement control unit 112 measures the user's biosignal using the data. According to the present exemplary embodiment of the present invention, a sensor unit 141 includes a pressure sensor, and is located between the radial artery 150 of the user's wrist and the cuff 140. Also, the biosignal may be the user's blood pressure. In this case, the sensor unit 141 senses pressure change of the cuff 140 by pressure which the micro pump 111 of the user's wrist applies, and displacement of the radial artery 150, and transduces the pressure change into an electric signal. Also, the measurement control unit 112 measures the user's blood pressure analyzing the electric signal depending on a predetermined algorithm. The sensor unit 141 measures the user's biosignal from a point in time when the pressure supplier 145 starts applying pressure to the user's wrist to a point in time when the pressure supplier 145 applies a maximum amount of pressure to the user's wrist. A method of measuring a user's biosignal sensing pressure change of the cuff 140 is described with reference to FIGS. 3 and 4.

Also, the sensor unit 141 further may include a pulse wave sensor measuring a user's pulse wave. In this case, the user's biosignal may be measured using a pulse wave measurement result measured using the pulse wave sensor, and pressure change of the cuff 140 measured using the pressure sensor.

According to another exemplary embodiment of the present invention, the measurement control unit 112 may transmit the transduced electric signal via a wired/wireless network to an external apparatus without performing a signal processing which measures a user's blood pressure. According to the present exemplary embodiment of the present invention, the measurement control unit 112 may be a communication interface unit transmitting the electric signal to the external apparatus designed according to a predetermined communication protocol. The external apparatus may be any one terminal of a terminal installed in a user's personal computer (PC), a hospital, and the like, a user's mobile communication terminal, and a mobile communication terminal of a user's family doctor. In this case, the electric signal transmitted from the measurement control unit 112 may measure the user's biosignal via a signal processing in the external apparatus. Since a structure of the communication interface, a communication protocol, and the like are not points of the present invention, a detailed description thereof is omitted.

A portable biosignal measurement apparatus according to the present invention is fastened around a user's wrist by a fastening unit 120. The fastening unit 120 may be embodied as a size that a general adult may wear around a wrist, and may have elasticity in order to closely adhere to the user's wrist. Although the fastening unit 120 is illustrated as a belt form in FIGS. 1A and 1B, the belt form is an example, and any form fastened around the user's wrist may be embodied.

Figure 2:
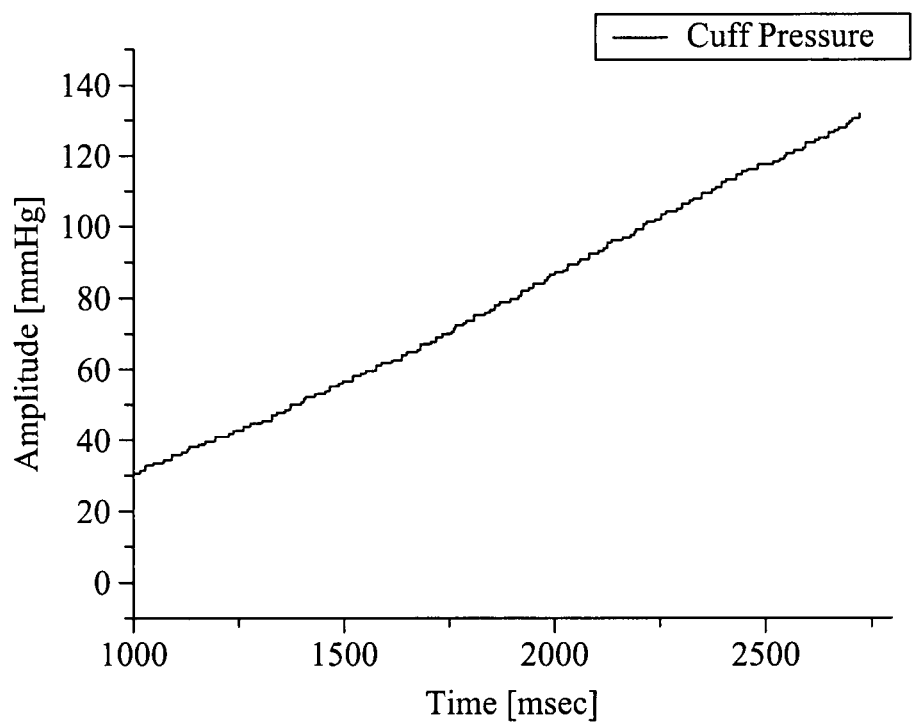
FIG. 2 illustrates pressure change applied to a cuff of a portable biosignal measurement apparatus according to an exemplary embodiment of the present invention.

FIG. 2 illustrates pressure change applied to a cuff 140 measured in a sensor unit of a portable biosignal measurement apparatus according to an exemplary embodiment of the present invention.

Figure 3:
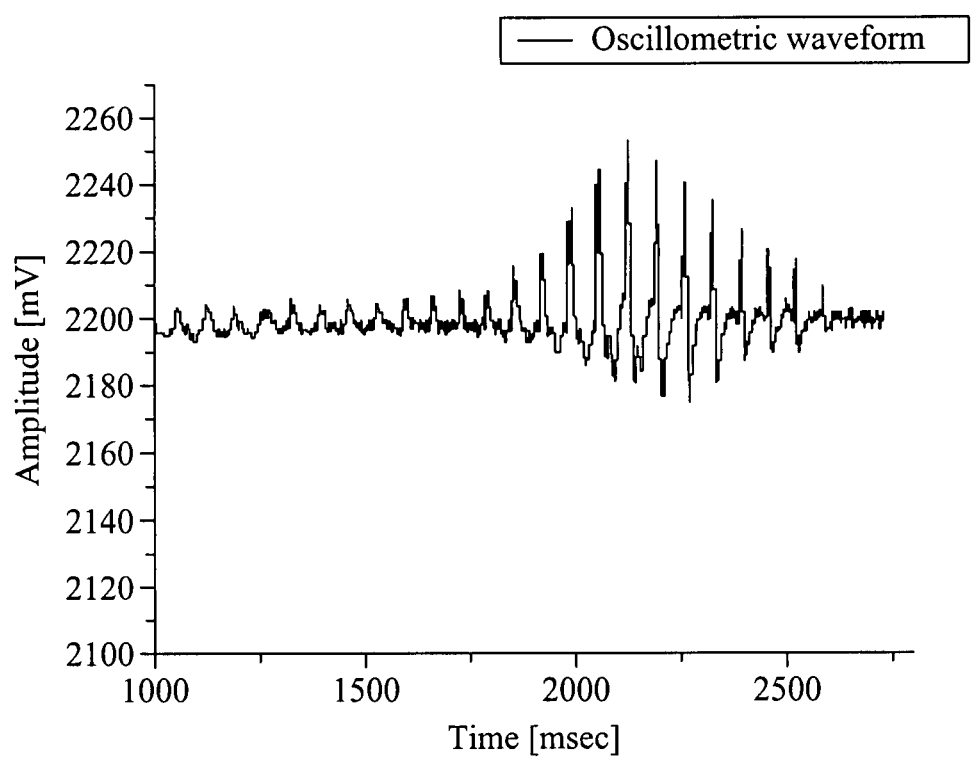
FIG. 3 illustrates an example of an oscillometric waveform obtained using the pressure change of the cuff illustrated in FIG. 2.

As illustrated in FIG. 1B, pressure is applied to the radial artery 150 of the user's wrist by pressure which the micro pump 111 applies. Pressure which the micro pump 111 applies, and in which an amplitude progressively increases during a predetermined period of time (for example, a period of time of blood pressure measurement), and minute pressure due to displacement of the radial artery 150 are added in the cuff 140. Therefore, a waveform in which minute noise is mixed is detected in the cuff 140, as illustrated in FIG. 2. Pressure change of the cuff 140 measured in the sensor unit 141 may be transduced into an electric signal, for filtering the transduced electric signal to obtain an oscillometric waveform measuring the user's blood pressure. FIG. 3 illustrates an example of an oscillometric waveform obtained using the pressure change of the cuff illustrated in FIG. 2.

Figure 4:
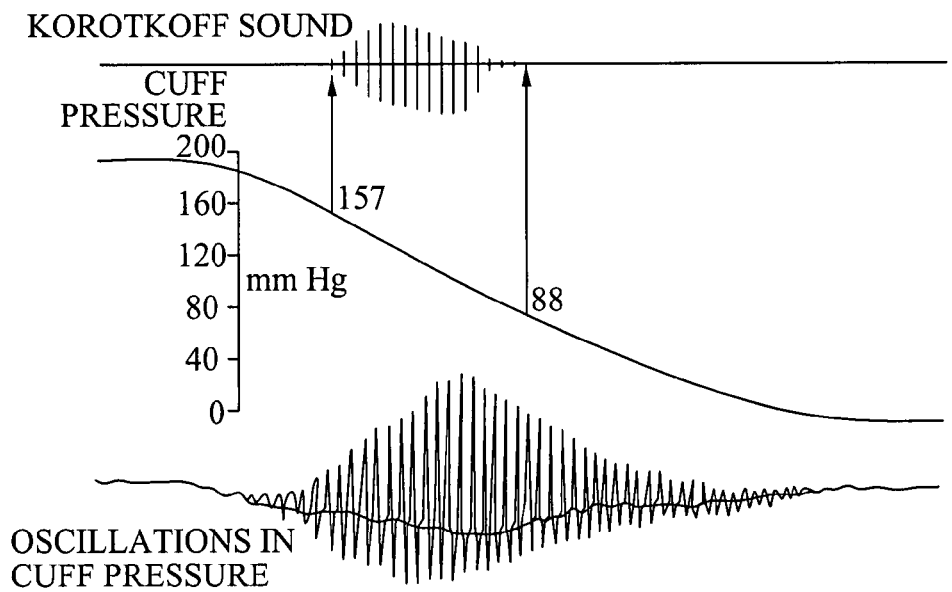
FIG. 4 illustrates an oscillometric method of measuring a user's blood pressure in a portable biosignal measurement apparatus according to an exemplary embodiment of the present invention.
Figure 4:
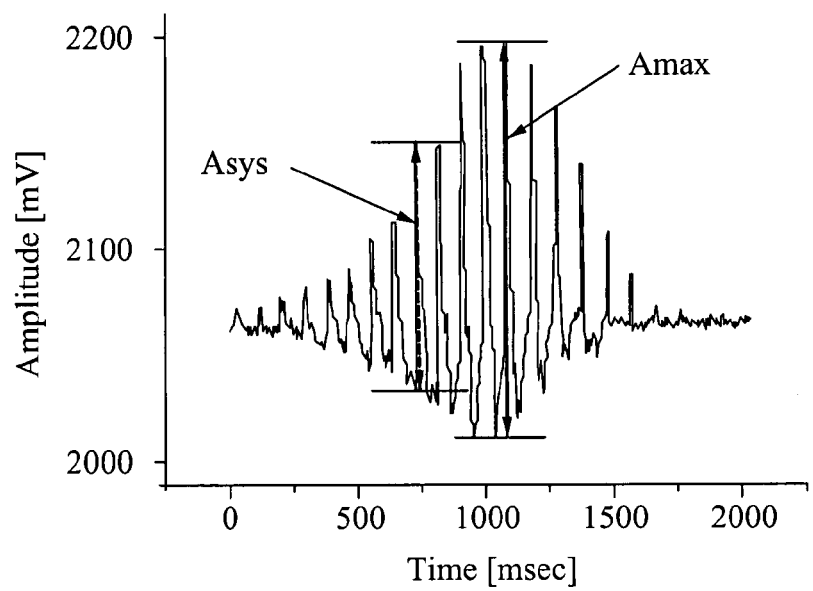

FIG. 4 illustrates an oscillometric method of measuring a user's blood pressure in a portable biosignal measurement apparatus according to an exemplary embodiment of the present invention. A top graph among the graphs illustrated in FIG. 4 shows a comparison result between a reference method and an oscillometric method. A bottom graph shows an example of using a characteristic ratio according to the oscillometric method.

The reference method applies pressure so that the pressure of a cuff, which surrounds a brachium, is greater than a systolic blood pressure, and measures the sound, which is caused by a blood flow during a decompression process, using a stethoscope. Specifically, a cuff pressure at a point in time when the sound is initially detected during the decompression process may be measured as the systolic blood pressure. The cuff pressure at a point in time when the sound disappears during the decompression process may be measured as a diastolic blood pressure.

The oscillometric method may utilize an identical procedure to the reference method, and measures an oscillation in a blood vessel during the procedure. Specifically, due to an arterial compliance characteristic, the oscillation in the blood vessel becomes a maximum when an intravascular pressure is equal to an extravascular pressure. Thus, the cuff pressure may be measured at a point in time corresponding to a certain ratio based on the amplitude of the maximum oscillation of the blood vessel. As shown in the bottom graph of FIG. 4, in the oscillometric method, the characteristic ratio may be set to Asys/Amax. The biosignal measurement apparatus according to the present invention may measure the blood pressure using the oscillometric method as described above.

According to the above-described exemplary embodiments of the present invention, there may be provided a portable biosignal measurement apparatus which can measure a biosignal by applying pressure to only a radial artery area of a user's wrist using a micro pump and a cuff, thereby improving a user convenience.

Also, according to the above-described exemplary embodiments of the present invention, there may be provided a portable biosignal measurement apparatus which a user can readily carry, since the size of the biosignal measurement apparatus is minimized, thereby conveniently and constantly measuring a biosignal.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A portable biosignal measurement apparatus to be worn by a user, the apparatus comprising:
    a control unit to control a fluid;
    a pressure supplier including a cuff to apply a pressure in a direction of a radial artery of the user's wrist by the fluid, which is flowed depending on the pressure;
    a fastening unit to fasten the portable biosignal measurement apparatus around the user's wrist when the apparatus is worn by the user;
    a support member, disposed on a portion of an upper surface of the fastening unit and a portion of a lower surface of the control unit; and
    a sensor unit to sense a biosignal using displacement of the radial artery,
    wherein the cuff is disposed between the support member and the sensor unit, and the support member supports the cuff to apply pressure in a direction of the radial artery, and
    wherein the control unit comprises a micro pump to apply pressure to the fluid using a motor, and a vessel to contain the fluid and to transfer the fluid from the vessel to the cuff by pressure which the micro pump applies using the motor,
    wherein the sensor unit includes a pressure sensor disposed between the cuff and the radial artery of the user when the apparatus is worn by the user, and
    the control unit houses the micro pump using the motor, the vessel containing the fluid, and a measurement control unit to measure the biosignal.

2. The apparatus of claim 1, wherein the measurement control unit further comprises a communication interface unit to transmit the measured biosignal to an external device.

3. The apparatus of claim 1, wherein the support member supports an upper surface and a lateral surface of the cuff to extend the cuff in the direction of the radial artery.

4. The apparatus of claim 1, wherein the fluid is air.

5. The apparatus of claim 1, wherein the pressure sensor is adapted to measure a pressure change of the cuff due to displacement of the radial artery, and the biosignal is blood pressure.

6. The apparatus of claim 1, further comprising:
    a measurement unit to measure the blood pressure based on the pressure change of the cuff.

7. The apparatus of claim 2, wherein the communication interface unit uses one of a wired and a wireless network to transmit the measured biosignal to the external device.

8. The apparatus of claim 1, wherein the sensor unit comprises:
    at least one pulse wave sensor to measure a pulse wave of the user's wrist from the radial artery.

9. The apparatus of claim 1, wherein the sensor unit is adapted to measure the user's biosignal from a point in time when the pressure supplier starts applying pressure to the user's wrist to a point in time when the pressure supplier applies a maximum amount of pressure to the user's wrist.

10. The apparatus of claim 1, wherein a size of the cuff is smaller than the user's wrist.

11. A method for measuring a biosignal, the method comprising:
    storing a fluid in a vessel of an article worn by a user;
    controlling a flow of the stored fluid from the vessel into a cuff portion of the article using a micro pump with a motor;
    applying a pressure in a direction of a radial artery of the user's wrist by the fluid transferred to the cuff, by using the micro pump with the motor to apply pressure to the fluid in the cuff;
    supporting the cuff by applying pressure in a direction of the radial artery, by using a support member disposed on a portion of an upper surface of a fastening unit which fastens the article around the user's wrist and a portion of a lower surface of a body housing the micro pump with the motor; and
    measuring a biosignal of the user, by using a sensor unit, wherein the cuff is disposed between the support member and the sensor unit, and the sensor unit includes a pressure sensor disposed between the cuff and the radial artery of the user, wherein the body housing the micro pump with the motor also houses the vessel containing the fluid and a measurement control unit to measure the biosignal.

12. The method of claim 11, further comprising transmitting the measured biosignal to an external device.

13. The method of claim 11, wherein the measuring the biosignal of the user comprises measuring a pulse wave of the user's wrist from the radial artery.

14. The method of claim 11, wherein the measuring the biosignal of the user comprises measuring the user's biosignal from a point in time when the applying pressure to the user's wrist starts, to a point in time when a maximum amount of pressure is applied to the user's wrist.

15. The apparatus of claim 1, wherein the control unit includes a frame to house the micro pump, the vessel containing the fluid, and the measurement control unit, the frame having an upper surface and a lower surface, wherein the support member includes an upper surface and a lower surface, and a portion of the lower surface of the support member is disposed adjacent to the portion of the upper surface of the fastening unit and a portion of the upper surface of the support member is disposed adjacent to a portion of the lower surface of the frame of the control unit.

16. The apparatus of claim 1, wherein the sensor unit transduces a pressure change of the cuff into an electric signal.

17. The apparatus of claim 16, wherein the measurement control unit is adapted to analyze the electric signal transduced by the sensor unit to measure the user's blood pressure.

* * * * *